(12) United States Patent
Tobjork et al.

(10) Patent No.: US 11,674,917 B2
(45) Date of Patent: Jun. 13, 2023

(54) SENSOR APPARATUS

(71) Applicant: Sumitomo Chemical Company Limited, Tokyo (JP)

(72) Inventors: Daniel Tobjork, Cambridgeshire (GB); Pascal Cachelin, Cambridgeshire (GB)

(73) Assignee: Sumitomo Chemical Co., Ltd., Tokyo (JP)

( * ) Notice: Subject to any disclaimer, the term of this patent is extended or adjusted under 35 U.S.C. 154(b) by 82 days.

(21) Appl. No.: 17/212,650

(22) Filed: Mar. 25, 2021

(65) Prior Publication Data
US 2021/0302346 A1 Sep. 30, 2021

(51) Int. Cl.
| | |
|---|---|
| G01N 27/12 | (2006.01) |
| B01J 20/18 | (2006.01) |
| F16K 11/00 | (2006.01) |
| G01N 1/22 | (2006.01) |
| G01N 1/24 | (2006.01) |
| G01N 27/00 | (2006.01) |

(Continued)

(52) U.S. Cl.
CPC ............. *G01N 27/12* (2013.01); *B01J 20/18* (2013.01); *F16K 11/00* (2013.01); *G01N 1/2205* (2013.01); *G01N 1/24* (2013.01); *G01N 27/005* (2013.01); *G01N 27/414* (2013.01); *G01N 33/004* (2013.01)

(58) Field of Classification Search
CPC .... G01N 27/12; G01N 27/414; G01N 33/005; G01N 33/004; G01N 27/122
USPC ....................................................... 73/31.06
See application file for complete search history.

(56) References Cited

U.S. PATENT DOCUMENTS

| | | | | |
|---|---|---|---|---|
| 5,502,659 A | * | 3/1996 | Braster | G01N 33/0006 73/1.06 |
| 2006/0272942 A1 | * | 12/2006 | Sirringhaus | G01N 27/414 204/406 |

(Continued)

FOREIGN PATENT DOCUMENTS

| | | | |
|---|---|---|---|
| CN | 108548855 A | * | 9/2018 |
| CN | 108548855 A | | 9/2018 |

(Continued)

OTHER PUBLICATIONS

Bingxue et al, 'Recent advances in detecting and regulating ethylene concentrations for shelf-life extension and maturity control of fruit: A review', Trends in Food & Science Technology 91 (2019) 66-82 (Year: 2019).*

(Continued)

*Primary Examiner* — Clayton E. LaBalle
*Assistant Examiner* — Kevin C Butler
(74) *Attorney, Agent, or Firm* — Wolf, Greenfield & Sacks, P.C.

(57) ABSTRACT

An apparatus for determining a presence, a concentration or a change in concentration of a target material in an environment is disclosed. The apparatus comprises first and second sensors configured to respond to the target material. The apparatus further comprises a fluid inlet in fluid communication with the environment, and a valve assembly having a first and second configuration. In the first configuration, the fluid inlet is in fluid communication with only the first sensor. In the second configuration, the fluid inlet is in fluid communication with the first sensor and the second sensor.

18 Claims, 7 Drawing Sheets

(51) Int. Cl.
*G01N 27/414* (2006.01)
*G01N 33/00* (2006.01)

(56) References Cited

U.S. PATENT DOCUMENTS

| | | | | |
|---|---|---|---|---|
| 2015/0123090 A1* | 5/2015 | Musiol | .................... | C09B 57/08 |
| | | | | 438/46 |
| 2020/0041443 A1* | 2/2020 | Newsome | .......... | G01N 27/4141 |
| 2020/0088674 A1* | 3/2020 | Tobjork | ................ | H01L 51/052 |
| 2020/0225186 A1* | 7/2020 | Goddard | ............. | H01L 51/0007 |
| 2020/0386702 A1* | 12/2020 | Godddard | .......... | G01N 33/0047 |
| 2020/0400600 A1* | 12/2020 | Tobjork | ............. | G01N 27/4163 |
| 2021/0302346 A1* | 9/2021 | Tobjork | ................. | G01N 27/12 |

FOREIGN PATENT DOCUMENTS

| | | | | |
|---|---|---|---|---|
| DE | 102013100950 A1 * | 7/2014 | ......... | G01N 33/0006 |
| DE | 102020213386 A1 * | 12/2021 | ......... | G01N 33/0029 |
| GB | 2593511 A * | 9/2021 | ............. | B01J 20/18 |
| GB | 2593547 A * | 9/2021 | ......... | G01N 33/0004 |
| WO | WO 2016/030386 A1 | 3/2016 | | |
| WO | WO-2016030386 A1 * | 3/2016 | ............. | B01D 46/42 |
| WO | WO-2018062503 A1 * | 4/2018 | ............... | G01N 1/00 |
| WO | WO-2021159180 A1 * | 8/2021 | | |
| WO | WO-2021185690 A1 * | 9/2021 | | |

OTHER PUBLICATIONS

Yongfang Li, Organic Optoelectronic Materials, Springer, 2015, vol. 91 3.22, p. 202 (Year: 2015).*

Kalpana et al., Printable ammonia sensor based on organic field effect transistor, Elsevier Organic Electronics 15, 2014, pp. 3221-3220 (Year: 2014).*

Hideki et al, Air-assisted High-performance Field-effect Transistor with Thin Films of Picene, J.Am. Chem. Soc, 2008, pp. 10470-10471 (Year: 2008).*

Combined Search and Examination Report dated Aug. 12, 2020 in connection with GB Application No. 2004342.8.

* cited by examiner

SENSOR APPARATUS

RELATED APPLICATIONS

This Application claims foreign priority benefits under 35 U.S.C. § 119(a)-(d) or 35 U.S.C. § 36(b) of British application number GB 2004342.8, filed Mar. 25, 2020, the entirety of which is incorporated herein.

BACKGROUND

Embodiments of the present disclosure relate to apparatus and methods for sensing a target gas in an environment. More particularly, but not by way of limitation, some embodiments of the present disclosure relate to apparatus and methods for sensing a 1-methylcyclopropene (1-MCP) and/or ethylene.

Thin film transistors (TFTs) have been previously used as gas sensors. For example, such use of thin film transistors as gas sensors is described in Feng et al, "Unencapsulated Air-stable Organic Field Effect Transistor by All Solution Processes for Low Power Vapor Sensing" Scientific Reports 6:20671 DOI: 10.1038/srep20671 and Besar et al., "Printable ammonia sensor based on organic field effect transistor", Organic Electronics, Volume 15, Issue 11, November 2014, Pages 3221-3230. In thin film transistor gas sensors, a semiconducting layer is in electrical contact with source and drain electrodes and a gate dielectric is disposed between the semiconducting layer and a gate electrode. Interaction of a target material with the TFT gas sensor may alter the drain current of the TFT gas sensor.

Metal oxide gas sensors have also been used to detect the presence of a target material in a gaseous environment. For example, metal oxide gas sensors have been described in Wang et al., "Metal Oxide Gas Sensors: Sensitivity and Influencing Factors", Sensors 2010, 10(3) 2088-2106 DOI: 10.3390/s100302088. Metal oxide gas sensors detect concentration of various types of gases by measuring the resistance change of the metal oxide due to adsorption of gases.

Ethylene produced by plants can accelerate ripening of climacteric fruit, the opening of flowers, and the shedding of plant leaves. 1-methylcyclopropene (1-MCP) is known for use in inhibiting such processes.

It may be desirable to determine the presence and/or concentration of certain materials in an environment. However, a sensor used for this purpose may respond to one or more materials in the environment other than the target material; the concentration of background materials in the environment that the sensor responds to may change over time; or the response of the sensor to a target or background material may change as the sensor ages.

SUMMARY

In some embodiments there is provided apparatus configured to determine a presence, a concentration or a change in concentration of a target material in an environment, which may be a gaseous or liquid environment. The apparatus comprises first and second sensors configured to respond to the target material. The apparatus further comprises a fluid inlet in fluid communication with the environment; and a valve assembly having a first and second configuration. When the valve assembly is in the first configuration, the fluid inlet is in fluid communication with only the first sensor. When the valve assembly is in the second configuration the fluid inlet is in fluid communication with the first sensor and the second sensor.

Optionally, the apparatus further comprises a first fluid flow path between the fluid inlet and the valve assembly, and the first sensor is disposed in the first fluid flow path. Optionally, the apparatus further comprises a second fluid flow path between the fluid inlet and the valve assembly. Optionally, the apparatus further comprises a third fluid flow path between the valve assembly and the second sensor.

Optionally, the apparatus further comprises a first fluid flow path between the fluid inlet and the valve assembly, a second fluid flow path between the fluid inlet and the first sensor and a third fluid flow path between the valve assembly and the second sensor.

Optionally, the apparatus further comprises a filter configured to remove the target material is disposed in the second fluid flow path.

Optionally, the filter comprises a molecular sieve.

Optionally, where the fluid is a gas, a desiccant is disposed in a dehumidification stage for dehumidification of gas drawn into the apparatus. The dehumidification stage may be disposed in the first fluid flow path between the fluid inlet and the first sensor and/or in the second or third fluid flow path between the fluid inlet and the second sensor.

Optionally, the dehumidification stage is disposed between the inlet and the valve assembly.

Optionally, in the case where the fluid is a gas, a humidification stage, e.g. comprising or consisting of a water reservoir, is disposed in the first fluid flow path between the desiccant and the first sensor and/or in the second or third fluid flow path between the desiccant and the second sensor. Optionally, the humidification stage may be disposed between the inlet and the first and/or second sensor. Optionally, a saturated salt solution is disposed in the humidifier or water reservoir.

Optionally, the valve assembly comprises a three-way valve.

Optionally, the gas is drawn from the environment using a pump.

Optionally, the first and/or second sensor is a thin film transistor or an organic thin film transistor.

Optionally, the first and/or second sensor is a metal oxide sensor, an electrochemical sensor, a photoionization sensor or an infrared sensor.

Optionally, the first and/or second sensor is a gas sensor.

According to some embodiments, there is provided a kit for forming the apparatus.

According to some embodiments, there is provided a system comprising a controller and the apparatus. The controller is operatively connected to the apparatus. The controller is configured to control the configuration of the valve assembly and/or monitor the presence, concentration or change in concentration of the target material.

According to some embodiments there is provided a method of determining a presence, concentration or change in concentration of a target material in an environment. The method comprises drawing gas from an environment into the apparatus. The method further comprises continuously measuring a response of the first sensor to a first gas from the environment from which any target material has not been removed. The method further comprises periodically switching the valve assembly between the first configuration and the second configuration. In the first configuration, the second sensor is in fluid communication with a second gas which does not contain the target material and in the second configuration the second sensor is in fluid communication with the first gas. The method further comprises measuring a response of the second sensor to the first gas; and applying a correction to the measurement of the first sensor in dependency on the measurement of the second sensor.

Optionally, the second gas is gas drawn from the environment from which any target material has been removed.

Optionally, the first and/or second gas is desiccated before reaching the first and/or second sensor.

Optionally, the target material is an alkene.

Optionally, the target material is 1-methylcyclopropene.

Optionally, the target material is ethylene.

DESCRIPTION OF THE DRAWINGS

The disclosed technology and accompanying figures describe some implementations of the disclosed technology.

Figure 1:
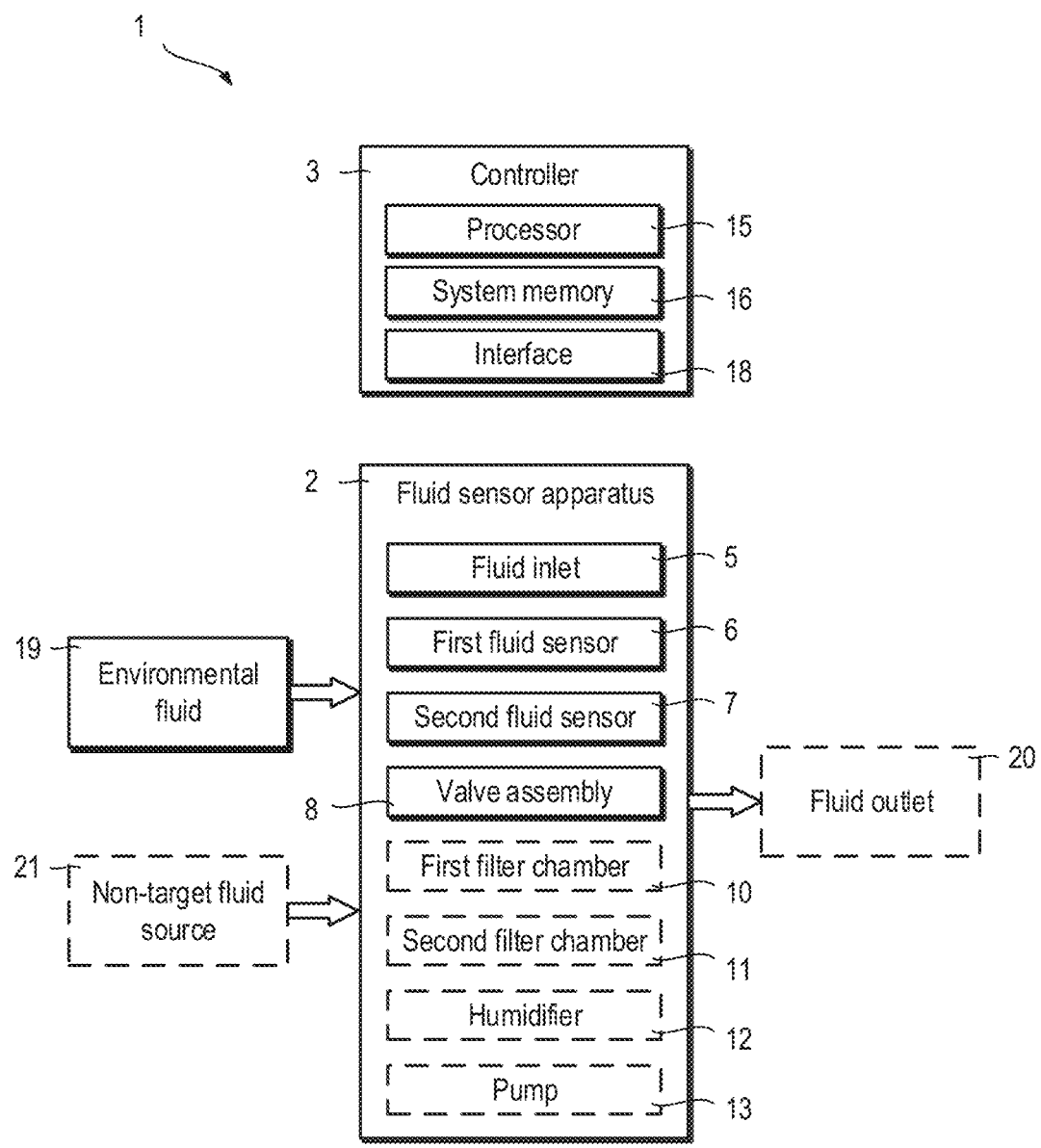
FIG. 1 illustrates a system for determining the presence, concentration or change in concentration of a target material in an environment.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology. Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

As used herein, by a material "over" a layer is meant that the material is in direct contact with the layer or is spaced apart therefrom by one or more intervening layers.

As used herein, by a material "on" a layer is meant that the material is in direct contact with that layer.

A layer "between" two other layers as described herein may be in direct contact with each of the two layers it is between or may be spaced apart from one or both of the two other layers by one or more intervening layers.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. The machine-readable medium includes non-transitory medium, where non-transitory excludes propagation signals. For example, a processor can be connected to a non-transitory computer-readable medium that stores instructions for executing instructions by the processor.

Sensors such as gas, liquid or particulate sensors may suffer from drift, i.e. the signal produced may change over time without any change in the environment (e.g. composition of the environment or changes in pressure or temperature). This may limit the lifetime of the sensor and/or accuracy of its measurements. The present inventors have found that changes arising for such drift may be compensated for using gas sensor apparatus and methods as described herein.

System Overview

Referring to FIG. 1, a sensor system according to some embodiments for sensing the presence, concentration or change in concentration of a target material in an environment, for example a gaseous or liquid environment, is shown. The system 1 includes a sensor apparatus 2 operatively connected to a controller 3. The sensor apparatus 2 includes a fluid inlet 5 for entry of environmental fluid into the apparatus; a first sensor 6; a second sensor 7 and a valve assembly 8 for controlling the flow of fluid through the apparatus 2. The first and second sensors 6, 7 are configured to respond to a target material in the environment. The target material may be a gas, a liquid, or a particulate in suspension in a fluid. The target material may be, for example, 1-methylcyclopropene (1-MCP) and/or ethylene.

Optionally the sensor apparatus 2 may include a filter chamber 10, which may include, for example a target material filter and/or, if the environment is a gaseous environment, a desiccant and a humidifier (e.g. a water reservoir) 12. The sensor apparatus may further include a pump 13 for pumping fluid through the apparatus 2. The controller 3 may further include a processor 15, system memory 16, and an interface 18 (e.g. a display) to allow the controller 3 to be programmed, for example, by a human. The controller may include additional peripheral devices for recording environmental conditions, for example, a thermometer (not shown) and a hygrometer (not shown) and the like.

A "valve" as used herein means any apparatus configured to allow or block fluid flow through the valve and may be manually operable (e.g. by way of a manually operable tap) and/or may be electromechanical, e.g. a solenoid valve, controllable by a controller 3, e.g. a programmable controller. For example the controller 3 may control the valve assembly 8 configuration. The controller may be programmable via the interface 18.

The sensor apparatus 2 may be in wired or wireless communication with a controller 3 configured to receive measurements from the first and/or second sensors 6, 7. The controller 3 may include a processor 15 which may be configured to determine the presence, concentration and/or change in concentration of the target material from the received sensor measurements. The system memory may store the sensor measurements, and/or other environmental information recorded by the system.

In the case where the target material is 1-MCP, the sensor apparatus may be configured to send a signal to the interface 18 or controller 3 if 1-MCP concentration as determined from measurements of the sensor apparatus falls below a threshold concentration. The controller 3 may be configured to activate a 1-MCP source for release of 1-MCP into the environment upon receiving a signal from the processor 18 that 1-MCP concentration has fallen below a threshold concentration.

The system 1 may further include a fluid outlet 20 for expelling fluid from the sensor apparatus 2. Optionally, the sensor system 1 is configured for fluid connection to a first material 21 which may be a non-target material source. The non-target material source may be a source of a fluid to which the sensor does not respond, for example nitrogen, and in which a sensor is able to desorb a target material.

Any suitable sensor may be used for either the first or second sensor 6, 7. For example, a sensor may be a thin film transistor (TFT), optionally an organic thin film transistor (OTFT). A TFT sensor as described herein may have a top gate, bottom gate or floating gate. A TFT sensor as described herein may have top or bottom source and drain contacts. A sensor as described herein may be a metal oxide sensor, a photoionisation sensor, an infrared sensor or electrochemical sensor. Further examples of suitable sensors include a pellistor sensor, an optical particle monitor, a quartz crystal microbalance sensor, a surface acoustic wave sensor, a cavity ring-down spectroscopy sensor or a biosensor. Some examples of suitable sensors can be found in WO 2019/063493 A1, the contents of which are incorporated herein by reference. The first and second sensors may be the same or different.

1-MCP has a slow adsorption and desorption of onto a Au surface (as measured by the induced work function shift by AC2). This has the effect that top-gate OTFT based 1-MCP sensors (with Au S/D contacts) may be slow to acclimatise to changes in 1-MCP concentration, for example between 100 ppb and 1000 ppb for 1-MCP. The conditions under which the 1-MCP concentration are typically measured, for example, when fruit (e.g. apples) are being loaded into a storage location or transportation vehicle, for example a shipping container, before the 1-MCP treatment is started, means there is likely to only be a limited time (e.g. <6 h) for acclimatising and measuring the baseline current of a sensor exposed to 1-MCP. There may also be to be changes in the background conditions (e.g. temperature and humidity) that may significantly affect the transistor current and eventually render the calculated concentration measurements logged over 24 h inaccurate.

Sensor Apparatus

Figure 2:
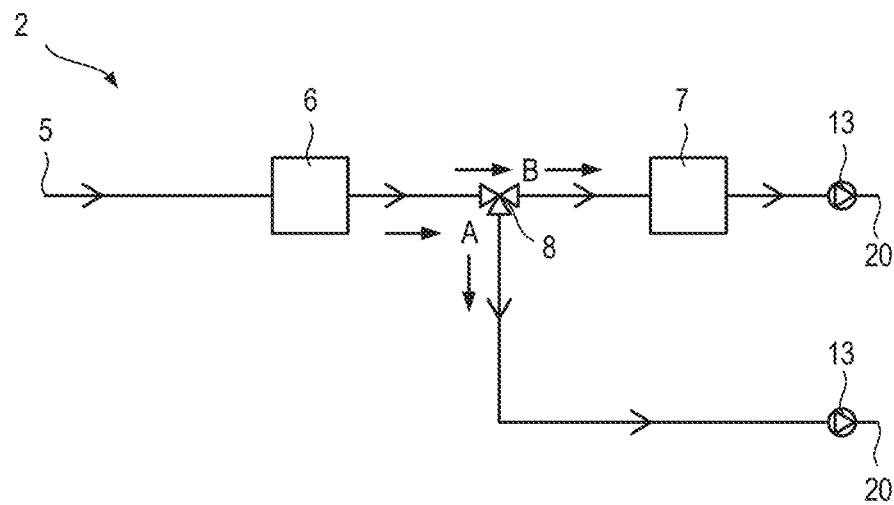
FIG. 2 illustrates a first sensor apparatus according to some embodiments in which a target material in a gas is continually sensed and periodically sensed.

Referring to FIG. 2, a first sensor apparatus 2 for determining a presence, a concentration or a change in concentration of a target material in an environment according to some embodiments of the present disclosure is shown. The first sensor apparatus includes first and second sensors 6, 7 configured to sense a target material in a environment, a fluid inlet 5 in fluid communication with the environment and a valve assembly 8 having a first and a second configuration. The valve assembly 8 may be, for example, a three-way valve, or a combination of two-way valves. The valve assembly 8 is disposed between the and first and second sensors 6, 7 or the inlet 5 and the first or second sensors 6, 7. When the valve assembly 8 is in the first configuration, marked 'A', only the first sensor 6 is in fluid communication with the fluid inlet 5. When the valve assembly 8 is in the second configuration, marked 'B', both the first and second sensors 6, 7 are in fluid communication with the fluid inlet 5.

The sensor apparatus 2 may be cycled between the first and second configuration.

The sensor apparatus 2 may be in a first configuration for a first time period T1. In the first configuration, the apparatus 2 defines a fluid flow path for flow of gas containing the target material from the inlet 5 to the first sensor 6 only. In the second configuration, the apparatus defines a fluid flow path for flow of gas containing the target material from the inlet 5 to both of the first sensor 6 and the second sensor 7.

As will be explained in more detail later, in use, when the sensor apparatus 2 is in the first configuration, gas enters the apparatus 2 from the environment via the inlet 5 and is in fluid communication with the first sensor 6. The first sensor 6 is exposed to the environment for the whole of the first time period T1. The measurement of responses of the first sensor 6 to the target material (if present) in the environment may be at any point during the first time period T1, for example, they may be once every one, 5, or 10 seconds, the measurements may be once every minute. The measurement responses of the first sensor 6 can measure the presence, concentration and/or change in concentration of a target material in the environment.

The sensor apparatus 2 may be in a second configuration for a second time period T2. In use, when the sensor apparatus 2 is in the second configuration, gas enters the apparatus 2 from the environment via the inlet 5 and is in fluid communication with both the first and second sensors 6, 7 in series, i.e., the gas enters the sensor apparatus 2 and is in contact with the first sensor 6 and then the second sensor 7. The second sensor 7 is exposed to the environment for the whole of the second time period T2. The measurement of responses of the first and second sensors 6, 7 to the target material in the environment may be at any point during the second time period T2, for example, they may be once every one, 5, or 10 seconds, the measurements may be once every minute. The measurement responses of the first and second sensors 6, 7 can measure the presence, concentration and/or change in concentration of a target material in the environment.

In both the first and second valve assembly 8 configurations, the gas may then pass out of the apparatus 2 via an outlet 20. Optionally, a pump 13 may be used to control the flow of gas through the apparatus 2. The rate of fluid flow through the environment may be less than 50 cm$^3$/min.

Typically, the first time period T1 is longer than the second time period T2. For example, the first time period T1 may be at least 10 times longer than T2, or at least 10 times longer than T2, or at least 100 times longer than T2; e.g. the first time period T1 may be 1 hour or more, and the second time period T2 may be 1 minute or less. With this arrangement, it is possible to both continually monitor the presence, concentration, and/or change in concentration of a target material present in an environment using the first sensor 6 and periodically monitor the presence, concentration, and/or change in concentration of a target material present in an environment using the second sensor 7. By periodically removing the target material from being in gaseous communication with the second sensor 7, the sensor may desorb the target material, for example, from the surface of an active part of the second sensor 7. The time taken for the target material to desorb from the sensor will depend at least on the type of target material and the type of sensor. The target material desorption time may be 30 minutes, or one hour, or may be greater than one hour. Thus, the second sensor 7 may not be subject to drift caused by the adsorption of the target material on the sensor. Therefore, the second sensor 7 may give a more accurate measurement of the target material in the environment during T2. A value measured by the second sensor 7 during T2 may be used to correct a value measured by the first sensor 6 during T1, e.g. to correct for drift caused by adsorption of the target material In some embodiments, the second sensor 7 of the sensor apparatus 2 may be in gaseous communication with a non-target material for some or all of the first period to aid desorption of the target material from the second sensor 7.

A measurement of a response of either the first sensor 6 to a target material in the environment is described herein as a "first sensor measurement" and a measurement of a response of the second sensor 7 to a target material in the environment is described hereinafter as a "second sensor measurement". The first and second sensor measurements may be taken in any order.

Figure 3:
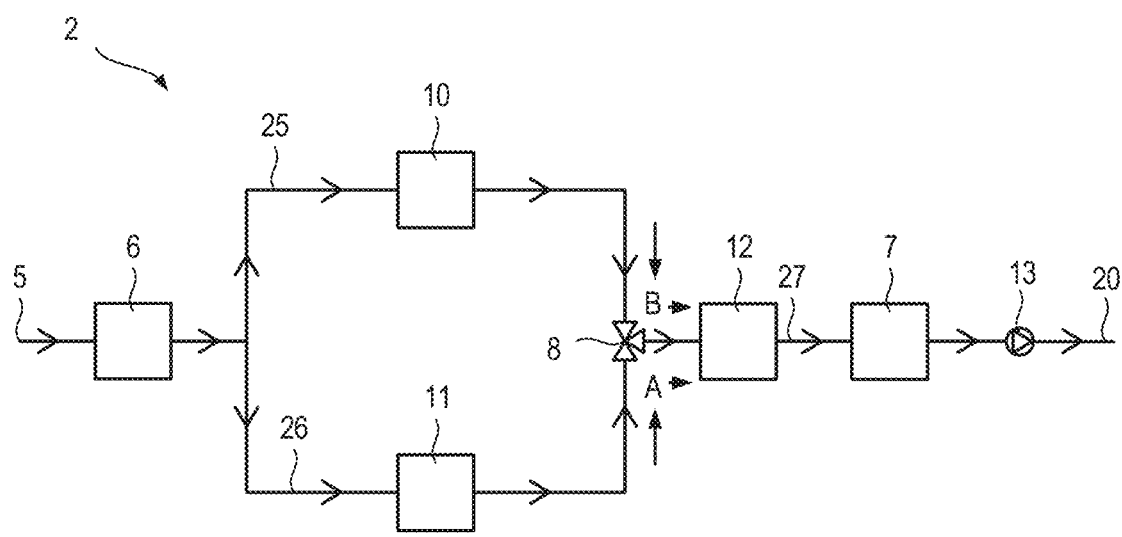
FIG. 3 illustrates a second sensor apparatus according to some embodiments in which a target material in a gas is continually sensed and periodically sensed.
Figure 4:
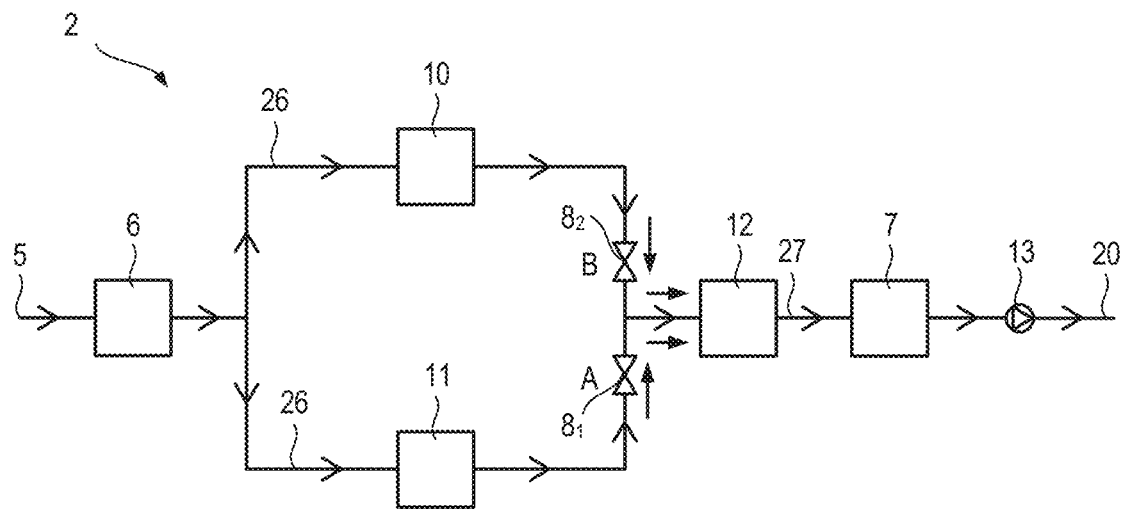
FIG. 4 illustrates a third sensor apparatus according to some embodiments in which a target material in a gas is continually sensed and periodically sensed.

Referring to FIGS. 3 and 4, in some embodiments, in use, in the first configuration 'A' the environment may be in fluid communication with the first sensor 6 and have a target material removed from the fluid before being in fluid communication with the second senor 7. In the second configuration 'B', the target material is not removed from the fluid before the fluid is in fluid communication with the second sensor 7.

In some embodiments, the sensor apparatus 2 may include one or more fluid flow junctions, e.g. 'T' junctions, directing the fluid to first, second and third flow paths 25, 26, 27. The first flow path 25 is arranged between the inlet 5 and the valve assembly 8 and the first sensor 6 is arranged in the first path 25 between the fluid inlet 5 and the valve assembly 8. The second flow path 26 is arranged between the fluid inlet 5 and the valve assembly 8. The third flow path 27 is arranged between the valve assembly and the second sensor 7. When in use, the valve assembly 8 may be configured to divert the flow of fluid through the sensor apparatus 2 so that the fluid flows through the first and then third flow paths 25, 27 or the second and then third flow paths 26, 27.

The valve assembly 8 may be, for example, a three-way valve as in the example in FIG. 3, or a combination of two-way valves, as in the example in FIG. 4. Referring in particular to FIG. 4, a first and second two-way valves $8_1$, $8_2$ may be arranged after a fluid flow junction in the direction of flow of the fluid, and before the second sensor 7. In the first configuration 'A', only the first two-way valve $8_1$ is open, and the second two-way valve $8_2$ is closed. In the second configuration 'B', the second two-way valve $8_2$ is open and the first two-way valve $8_1$ is closed.

Fluid flowing along the first fluid flow path 25 may pass through or over a filter in a filter region of the first fluid flow path 25 between the valve assembly 8 and the fluid inlet 5. The filter may be a filter material, a filter mesh, a chemical filter, a scrubber or a filter device and the like. If the fluid is a gas, the filter may include or be replaced with a desiccant and/or dehumidifier. The desiccant or dehumidifier may be a molecular sieve or a solid metal salt. A suitable filter will be selected according to the material needed to be removed or reduced in concentration.

If the filter comprises or consists of a desiccant, the desiccant may selectively remove water only from the gas. In some embodiments, the desiccant is a molecular sieve which may have a size selected to remove water but not a target material, e.g. a molecular sieve having a pore size of less than 4 Å, e.g. 3 Å if the target gas is an organic compound such as an alkene, e.g. 1-MCP or ethylene; an alcohol, e.g. ethanol; or CO2. The desiccant may be a solid state salt. The salt may be an ammonium, alkali, alkali earth or transition metal salt. The salt may be, without limitation, a halide, hydroxide, sulfate, acetate, dichromate, formate or nitrate. Exemplary salts include, without limitation, $NH_4NO_3$, $(NH_4)_2SO_4$, LiCl, NaCl, $MgCl_2$, KCl, KOH, KBr, KI, NaBr, $Mg(NO_3)_2$, $NaNO_3$, $KNO_3$, sodium or potassium acetate, sodium or potassium dichromate, calcium formate and copper sulfate.

In some embodiments, the first sensor which has a continuous exposure to the target material may be a robust and/or stable sensor (for example, a metal oxide-base sensor or a photoionisation detector) but may have a lower accuracy and/or selectivity for sensing the target material. The second sensor which is periodically exposed to a target material may be a sensor which is less stable and/or robust (e.g. an electrochemical sensor, or a field effect transistor-based sensor) but may be more accurate and/or selective to the same target material.

Metal oxide and photoionisation detectors may function most effectively in a dry environment. Accordingly, in some embodiments gas drawn into apparatus comprising a metal oxide sensor or photoionisation detector may be dehumidified by at least one of a material which removes water but not the target material and a filter material which removes both of water and the filter material, but not rehumidified before reaching the gas sensor.

Electrochemical sensors may provide more stable signals and/or have longer lifetime if exposed non-continuously to a target gas as described herein.

The filter may be disposed in a first filter chamber 10 having an inlet and outlet in fluid communication with the first fluid flow path 25. The first filter chamber 10 may be removable and/or may have a sealable opening, e.g. for replacement of the filter therein. In some embodiments, the first filter chamber 10 is disposed between the fluid inlet 5 and the first sensor 6. In some embodiments, a filter chamber 10 may be placed between the fluid inlet 5 and/or the first or second sensor 6, 7.

In some embodiments, the filter in the first filter chamber 10 is a molecular sieve. The average pore size of the molecular sieve may be selected according to the requirements of the filter in the system. In the case of a filter to remove water, the molecular sieve optionally has a pore size of at least 3 Å.

Fluid flowing along the second fluid flow path 26 may pass through or over a filter in a filter region of the second fluid flow path 26 between the valve assembly 8 and the fluid inlet 5. If the fluid is a gas, the filter may include or be replaced with a desiccant. The filter may be disposed in a second chamber 11 having an inlet and outlet in fluid communication with the second fluid flow path 26. The second filter chamber 11 may be removable and/or may have a sealable opening, e.g. for replacement of the filter therein.

The filter in the second filter chamber 11 may adsorb or absorb the target material. The filter may react with the target material.

In some embodiments, the filter in the second filter chamber 11 selectively removes only the target material (if present) from the fluid it is exposed to.

In some embodiments, the filter in the second filter chamber 11 selectively removes the target material and one or more further materials from the fluid it is exposed to. If the fluid entering the sensor apparatus 2 is a gas, the filter in the second filter chamber 11 may be a desiccant, e.g. silica gel, which removes water in addition to the target material. The present inventors have found that silica gel may be used to withdraw both water and 1-MCP from an environment.

In some embodiments, the filter in the second filter chamber 11 is a molecular sieve. The average pore size of the molecular sieve may be selected according to the target material. In the case of a volatile organic compound, e.g. 1-MCP, the molecular sieve optionally has a pore size of at least 4 Å, optionally at least 5 Å or 10 Å.

In some embodiments, the filter material is active carbon. Filtering of the target material has been described above with reference to a filter material.

In other embodiments, a filter device, e.g. a mesh or HEPA filter for a particulate target material or a scrubber for a target compound, may be used.

In some embodiments, if the fluid is a gas, fluid flowing along the third flow path 27 may pass through a humidification stage (e.g. a water reservoir) 12, before the fluid is in fluid communication with the second sensor 7. The re-humidification of the fluid flowing through the system is optional. Humidity can be controlled to a suitable level by using a saturated salt solution (e.g. NaCl for relative humidity of ~76%). This humidification allows the control of the humidity of the fluid before it reaches the second sensor, which may eliminate any differences in humidity between fluid flowing along the first fluid flow path 25 and the second fluid flow path 26 and/or reduce or eliminate any changes in measured values arising from changes in atmospheric humidity. In some embodiments, the humidification stage may comprise a gel humidifier. The gel may or may not contain a salt. A preferred humidity of a gas reaching the first or second sensor is in the range of 60-95% in the case where the sensor is an organic thin film transistor.

Figure 5:
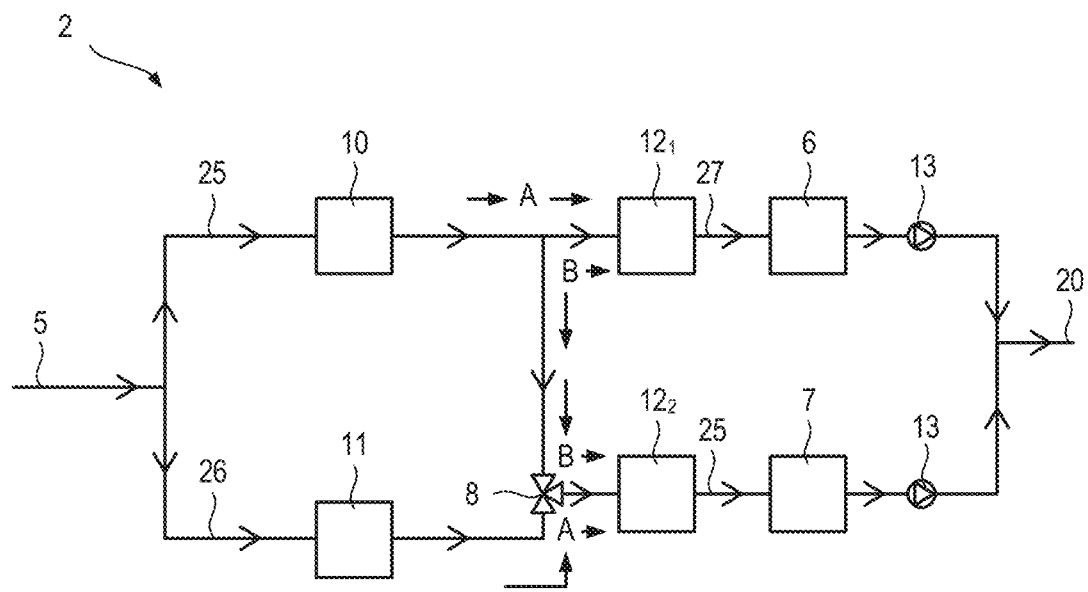
FIG. 5 illustrates a fourth sensor apparatus according to some embodiments in which a target material in a gas is continually sensed and periodically sensed.

Referring to FIG. 5, in some embodiments, the first and second sensors 6, 7 are arranged in parallel within the sensor apparatus 2, i.e. the same fluid does not flow through both the first and second sensors 6, 7. In use, the fluid is divided into first and second parallel flow paths 25, 26 after the fluid entered the apparatus 2 via the inlet 5. The second flow path 26 includes a filter for removing the target material between the inlet and the valve assembly 8. The first flow path may include a desiccant and/or filter and/or humidifier between the inlet 5 and the first sensor 6. A fluid flow junction is arranged in the first flow path, after the desiccant, if present. A first path from this junction is disposed between the junction and the valve assembly 8, and a second path is disposed between the junction and the first sensor 6.

In use, the valve assembly 8 in a first configuration 'A' allows the fluid with the target material to be in fluid communication with the first sensor 6, and the target to be removed from the fluid before the fluid is in fluid communication with the second sensor 7. In a second configuration 'B', the means for removing the target material, for example a filter, from the fluid before it is in fluid communication with the second sensor 7 is bypassed, allowing the second sensor to measure the presence, concentration, and/or change in concentration of the target material.

In some embodiments, the valve assembly 8 may be configured to allow the second sensor 7 to be in fluid communication with a fluid source 21 not containing the target material during the first time period. This may aid desorption of target material from the second sensor 7.

One-way valves (not shown) may be disposed along the flow paths to prevent fluid from flowing towards the inlet 5.

For example one-way valves may be disposed before and/or after the humidifier 12, sensors 6, 7, and/or filter compartments 10, ii.

In some embodiments a desiccant and a humidifier may be disposed in one or each flow path before the first and/or second sensor 6, 7. If the environment being monitored by the first and second sensors is a gas, some sensors may operate better (e.g. with greater accuracy, sensitivity of longevity) within certain humidity ranges.

Figure 6:
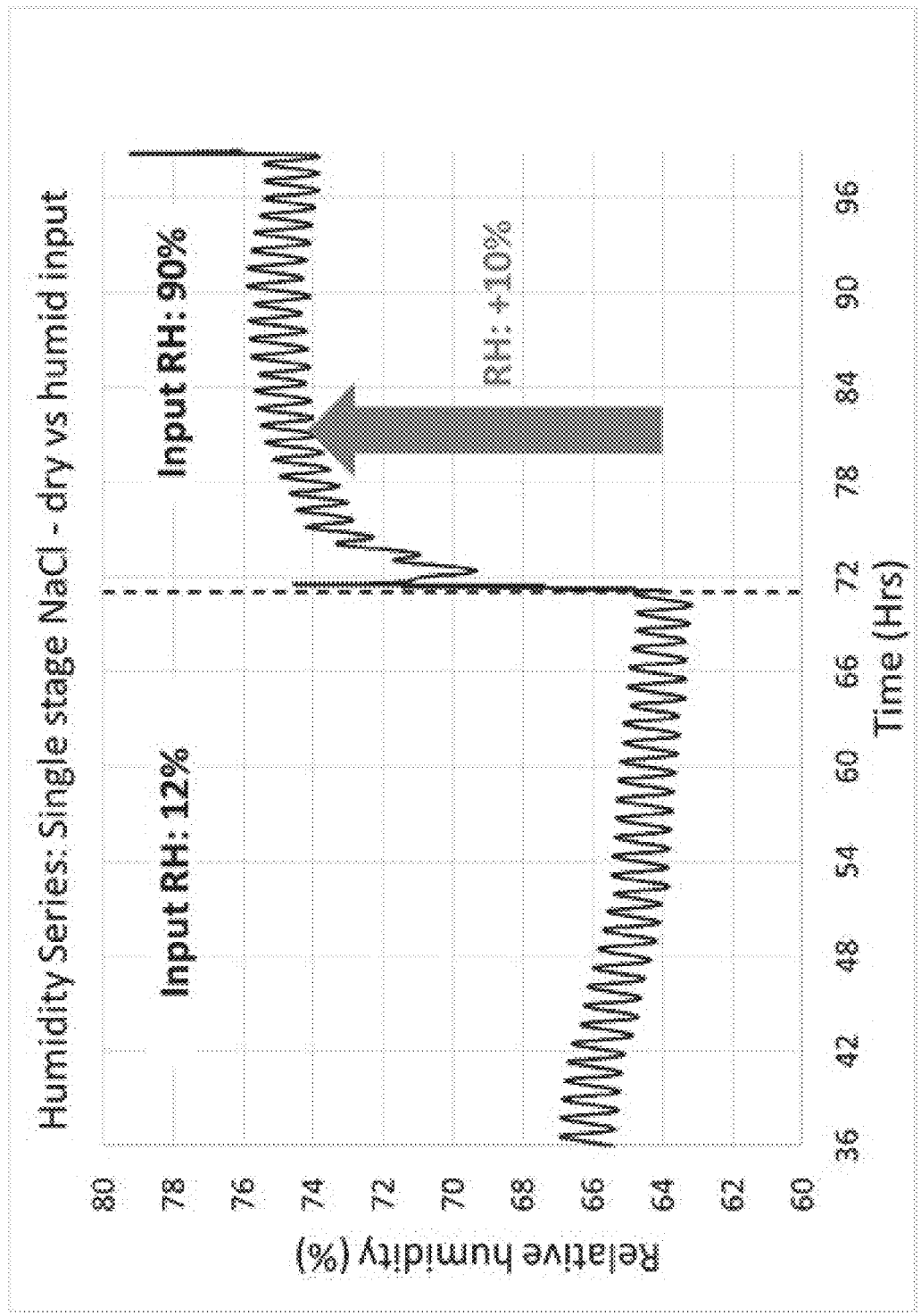
FIG. 6 is a graph of humidity of an output gas following humidification only of an input gas.

With reference to FIG. 6, changing input air from about 25% humidity to about 90% humidity is accompanied by an increase of about 10% in humidity of the output air.

Figure 7:
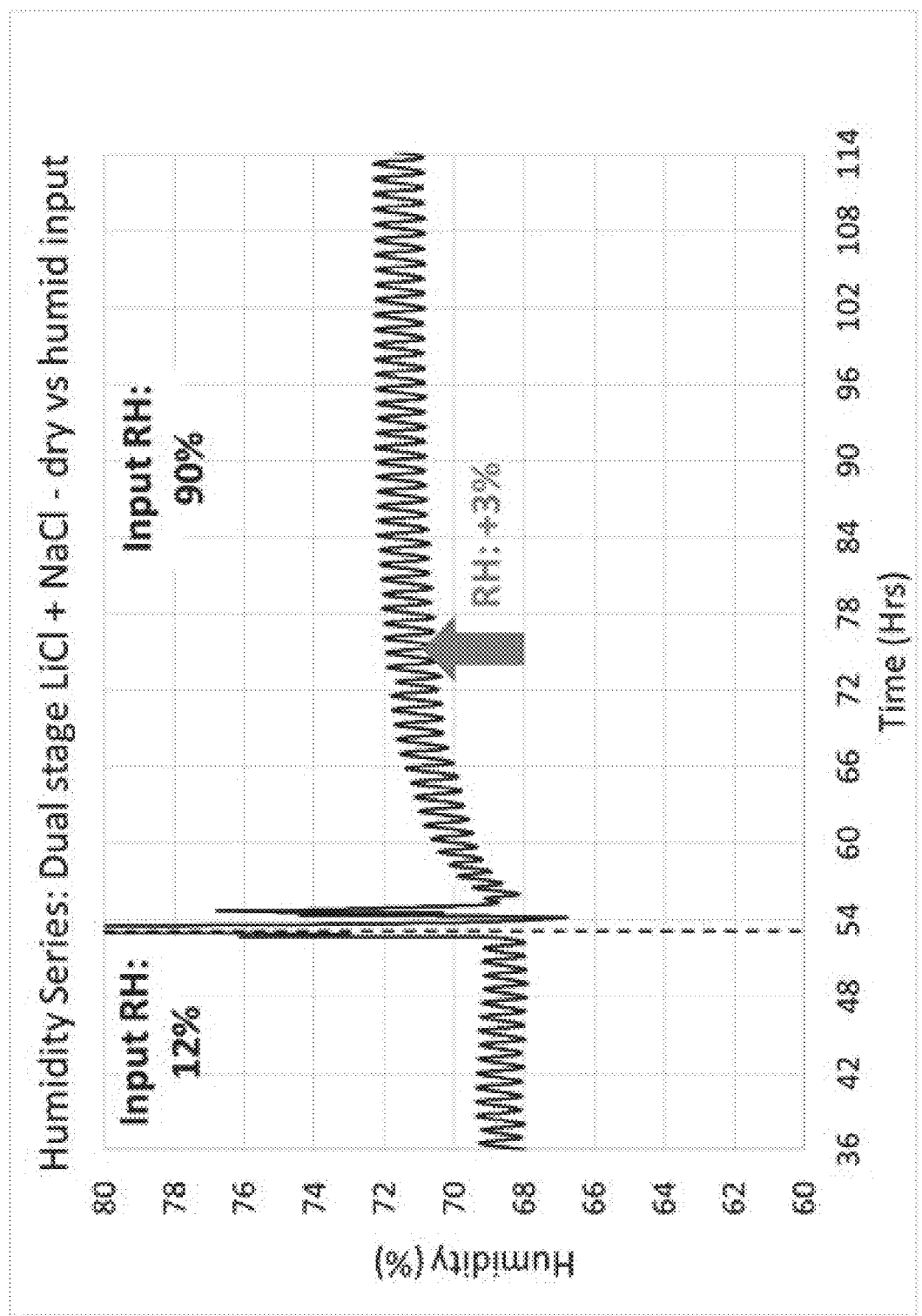
FIG. 7 is a graph of humidity of an output gas following dehumidification and rehumidification of an input gas.

With reference to FIG. 7, changing input air from about 25% humidity to about 90% humidity is accompanied by a much smaller change in humidity (about 3%) of the output air. The gas sensor apparatus and method as described herein may be used in monitoring the concentration of a target material in an environment in which the target material concentration is allowed to change naturally in the environment or in which the target material is artificially introduced or removed from the environment, e.g. introduction of 1-MCP into an environment, which may result in an irregular change in concentration of the gas over time.

Concentration Measurement

Figure 8:
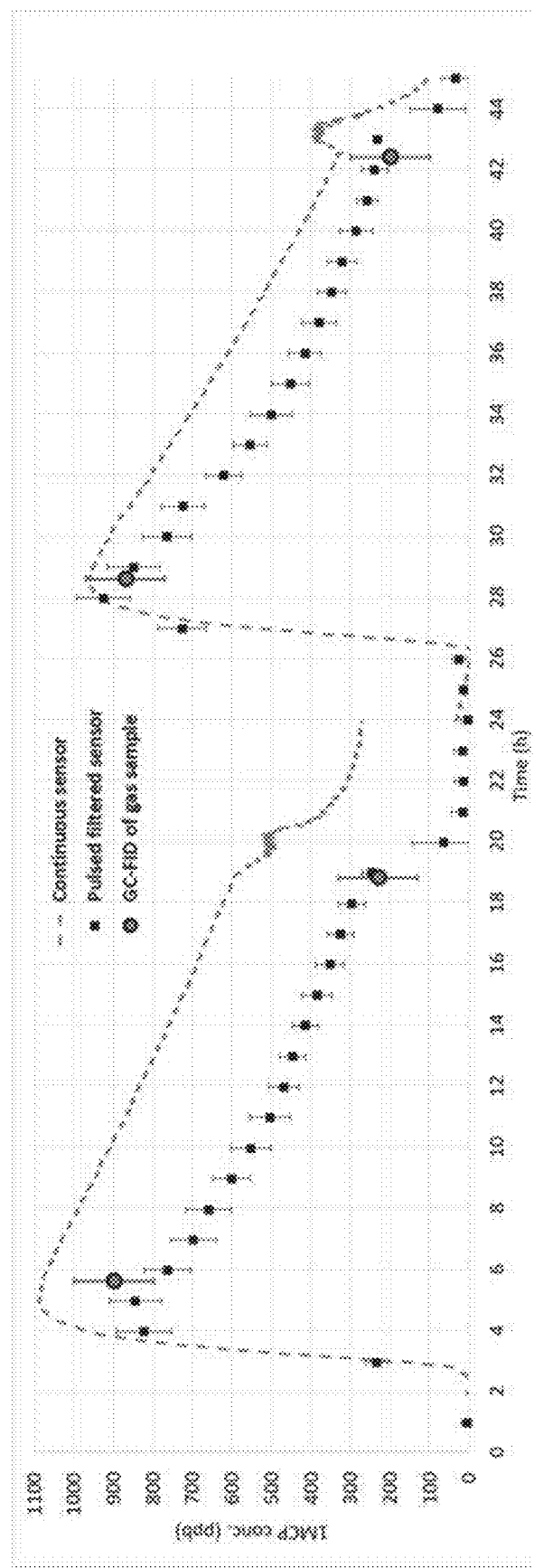
FIG. 8 illustrates a graph of 1-MCP concentration vs. time for a continuous measurement first sensor, a periodic measurement second sensor and reference measurements.

Referring to FIG. 8, the continuous first sensor measurement of the concentration of 1-MCP and the periodic second sensor measurement, once per hour, of the concentration of 1-MCP is plotted against time. The plot also includes reference measurements taken using Gas Chromatography with a Flame Ionisation Detector (GC-FID). The periodic measurements form the second sensor 7 are closer to the reference measurements taken using Gas Chromatography. It can be seen that the measurements from the first sensor 6 are prone to drift and do not accurately record the concentration of 1-MCP. Using a sensor apparatus 2 having both continuous and periodic measurements of target material concentrations allows the correction and/or calibration of the continuous measurement. Thus, the effect of drift in the sensor measurements may be controlled for.

Method of Operation

Figure 9:
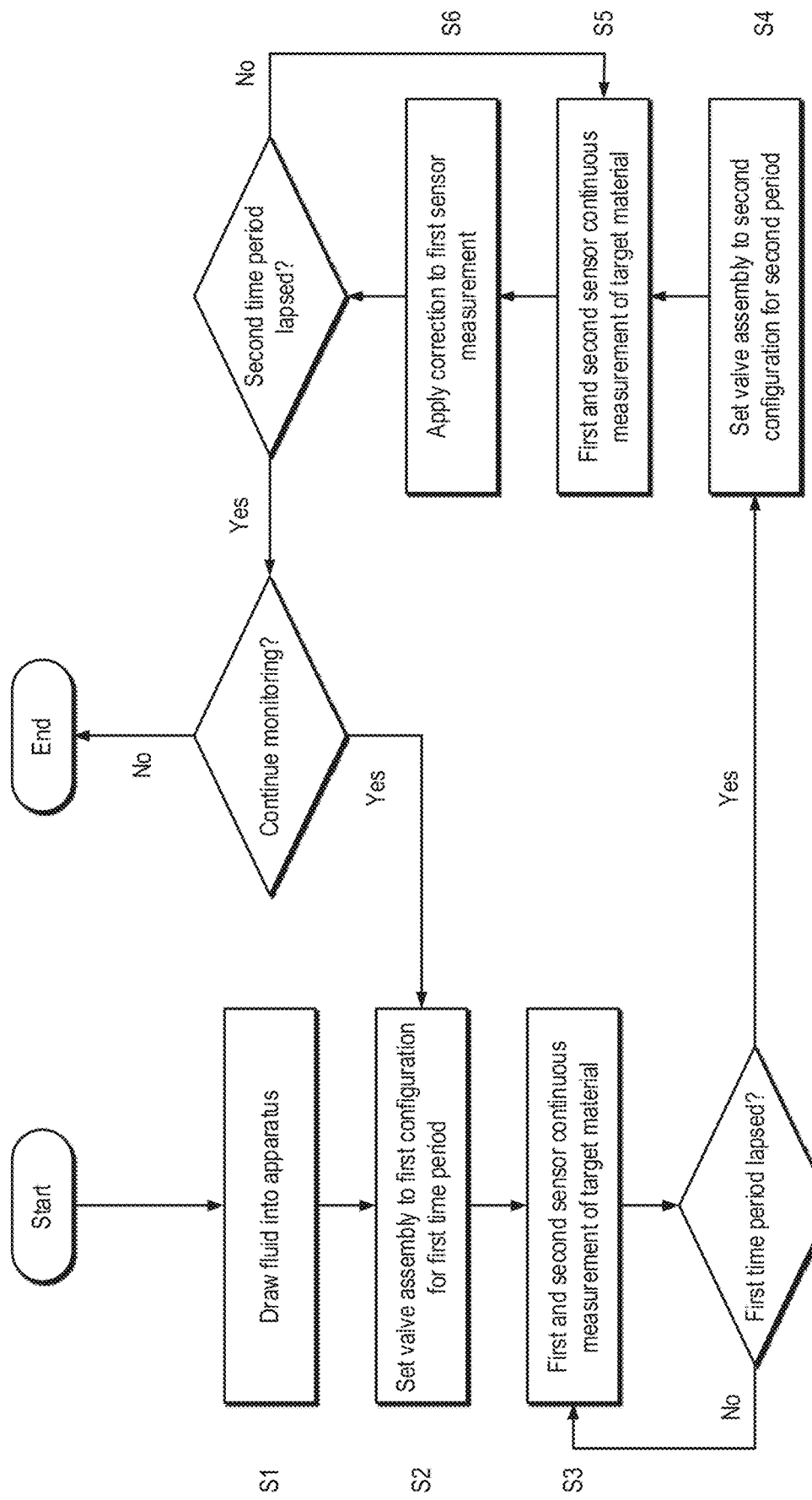
FIG. 9 is a process flow diagram according to some embodiments for determining the presence, concentration or change in concentration of a target material in an environment using measurements of a sensor apparatus in first and second configurations.

Referring to FIG. 9, to operate the sensor apparatus 2, fluid from a fluid source 19 is drawn into the apparatus via fluid inlet 5 (step S1). The valve assembly 8 is set to the first configuration 'A' for a first time period T1 to allow the first sensor 6 to be in fluid communication with the environment (step S2). In some embodiments, the first configuration 'A' allows both the first and second sensors 6, 7 to be in fluid communication with the environment, but the target material is removed from the fluid (for example, by a filter) prior to the fluid being in fluid communication with the second sensor 7. A first sensor measurement is continuously taken from the first sensor during the first time period T1 (step S3) which measures the presence, concentration or change in concentration of a target material in the environment. In some embodiments, a second sensor measurement may be taken from the second sensor 7, during the first time period T1, and can monitor the desorption rate of the target material from the sensor 7. When the first time period T1 has lapsed, the valve assembly 8 is set to the second configuration 'B' for a second time period T2. In the second configuration 'B', both the first and second sensors are in fluid communication with the environment, and no target material has been filtered form the fluid (step S4). First and second sensor measurements are recorded form the first and second sensors 6, 7 respectively throughout the second time period T2 (step S5). If required, a correction may be applied to the measurement of the first sensor 6 in dependency on the measurement of the second sensor 6 (step S6). The apparatus can be cycled between the first and second valve configurations for the first and second time periods respectively.

The invention claimed is:

1. Apparatus configured to determine a presence, a concentration or a change in concentration of a target material in an environment comprising:
   first and second sensors configured to respond to the target material;
   a fluid inlet in fluid communication with the environment;
   a valve assembly having a first and second configuration, wherein in the first configuration, the fluid inlet is in fluid communication with only the first sensor; and in the second configuration, the fluid inlet is in fluid communication with the first sensor and the second sensor;
   a first fluid flow path between the fluid inlet and the valve assembly, wherein the first sensor is disposed in the first fluid flow path;
   a second fluid flow path between the fluid inlet and the valve assembly; and
   a third fluid flow path between the valve assembly and the second sensor.

2. Apparatus according to claim 1 wherein a filter configured to remove the target material is disposed in the second fluid flow path.

3. Apparatus according to claim 2, wherein the filter comprises a molecular sieve.

4. Apparatus according to claim 1, wherein the fluid is a gas and a desiccant is disposed in the first fluid flow path between the fluid inlet and the first sensor and/or in the second and/or third fluid flow path between the fluid inlet and the second sensor.

5. Apparatus according to claim 4 wherein a humidifier is disposed in the first fluid flow path between the desiccant and the first sensor and/or in the second and/or third fluid flow path between the desiccant and the second sensor.

6. Apparatus according to claim 1, wherein the valve assembly comprises a three-way valve.

7. Apparatus according to claim 1, wherein the fluid is drawn from the environment using a pump.

8. Apparatus according to claim 1, wherein the first and/or second sensor is a thin film transistor.

9. Apparatus according to claim 1, wherein the first and/or second sensor is an organic thin film transistor.

10. Apparatus according to claim 1, wherein the first and/or second sensor is a metal oxide sensor.

11. A kit for forming apparatus according to claim 1.

12. A system comprising:
    a controller;
    the apparatus according to claim 1, wherein the controller is operatively connected to the apparatus; and
    the controller is configured to control the configuration of the valve assembly and/or monitor the presence, concentration or change in concentration of the target material.

13. The method according to claim 12 wherein the second fluid is fluid drawn from the environment from which any target material has been removed.

14. A method of determining a presence, concentration or change in concentration of a target material in an environment, the method comprising:
    drawing fluid from an environment into apparatus according to claim 1;
    continuously measuring a response of the first sensor to a first fluid from the environment from which any target material has not been removed;

periodically switching the valve assembly between the first configuration and the second configuration wherein: in the first configuration, the second sensor is in fluid communication with a second fluid which does not contain the target material and in the second configuration the second sensor is in fluid communication with the first fluid;

measuring a response of the second sensor to the first fluid; and applying a correction to the measurement of the first sensor in dependency on the measurement of the second sensor.

15. The method according to claim 14 wherein the first and/or second fluid is a gas and is desiccated before reaching the first and/or second sensor.

16. The method according to claim 14 wherein the target material is 1-methylcyclopropene.

17. The method according to claim 14 wherein the target material is ethylene.

18. Apparatus configured to determine a presence, a concentration, or a change in concentration of a target material in an environment, comprising:

first and second sensors configured to respond to the target material;

a fluid inlet in fluid communication with the environment;

a valve assembly having a first and second configuration, wherein in the first configuration, the fluid inlet is in fluid communication with only the first sensor, and in the second configuration, the fluid inlet is in fluid communication with the first sensor and the second sensor;

a first fluid flow path between the fluid inlet and the valve assembly;

a second fluid flow path between the fluid inlet and the first sensor; and a third fluid flow path between the valve assembly and the second sensor, wherein in the first configuration the apparatus is configured to allow fluid to flow through the second flow path, and in the second configuration, the apparatus is configured to allow fluid to flow through the first and third flow paths.

* * * * *